United States Patent [19]

Murtha et al.

[11] 4,094,918

[45] June 13, 1978

[54] HYDROALKYLATION PROCESS USING MULTI-METALLIC ZEOLITE CATALYST

[75] Inventors: Timothy P. Murtha; Ernest A. Zuech, both of Bartlesville, Okla.

[73] Assignee: Phillips Petroleum Company, Bartlesville, Okla.

[21] Appl. No.: 767,413

[22] Filed: Feb. 10, 1977

[51] Int. Cl.² .............................................. C07C 15/00
[52] U.S. Cl. ........................... 260/668 R; 260/668 B; 252/455 Z
[58] Field of Search ........... 260/668 R, 668 A, 668 B; 208/111, 120

[56] References Cited

U.S. PATENT DOCUMENTS

| | | | |
|---|---|---|---|
| 3,140,253 | 7/1964 | Plank et al. | 208/120 |
| 3,318,802 | 5/1967 | Martin | 208/111 |
| 3,642,925 | 2/1972 | Rausch | 260/668 A |
| 3,839,477 | 10/1974 | Suggitt et al. | 260/668 R |

*Primary Examiner*—Veronica O'Keefe

[57] ABSTRACT

An aromatic hydrocarbon is contacted under hydroalkylation conditions and in the presence of hydrogen with a composition comprising at least one rhodium or palladium compound or mixture thereof supported on a calcined, acidic, nickel and rare earth-treated crystalline zeolite.

14 Claims, No Drawings

HYDROALKYLATION PROCESS USING MULTI-METALLIC ZEOLITE CATALYST

The invention relates to a hydroalkylation process, a composition useful as a catalyst in said process and a method for producing said composition.

Prior art catalysts in the field of hydroalkylation processes suffered from several drawbacks. These deficiencies of the prior art catalysts for the hydroalkylation reaction included: (1) The use of support materials for certain catalysts which are not able to withstand the temperatures employed in a typical air burn-off regeneration operation. Such regeneration operations are commonplace in the catalytic art for hydrocarbon conversions of various types and it is highly desirable that the catalyst for the hydroalkylation process be stable to such typically employed regeneration conditions. (2) Productivity is rather low as judged by the low liquid hourly space velocities (LHSV) that are utilized in the prior art. Thus a more active and more selective hydroalkylation catalyst is desired. (3) A number of the catalysts of the prior art for the hydroalkylation reaction are prepared by very complex and time consuming processes. For example, starting with a powdered crystalline zeolite support, said support is cation exchanged, washed and then incorporated into a matrix of another material such as silicaalumina. This combination is calcined, cooled, and impregnated with certain metal salts. Finally the composite is extruded into pellets and the like. Thus it is desirable that a more simplified and less expensive process for making active and selective catalysts be found. (4) Certain catalysts of the prior art for the hydroalkylation reaction were of fixed acidity because of the type of support material utilized. This left little variation that could be made in this important property of the hydroalkylation catalyst. It is therefore desirable that catalysts be developed which are varied easily in their acidity characteristics.

It is an object of the present invention to hydroalkylate aromatic compounds. Another object of the present invention is to provide a method for producing a composition useful as a hydroalkylation catalyst.

Another object of the invention is a composition useful as a catalyst in hydroalkylation reactions which is regenerated by air burn-off.

Another object of the invention is a composition useful as a catalyst in hydroalkylation reactions which is more active and more selective than prior art catalysts.

Another object of the invention is a composition useful as a catalyst in hydroalkylation reactions which is simpler and less expensive to produce as compared to prior art catalysts.

Still another object of the invention is a composition useful as a catalyst in hydroalkylation reactions in which the acidity of the catalyst can be adjusted.

SUMMARY

According to the invention an aromatic hydrocarbon is contacted under hydroalkylation conditions and in the presence of hydrogen with a composition comprising at least one rhodium or palladium compound or mixture thereof supported on a nickel and rare earth-treated crystalline zeolite support which is calcined to produce an acidic support before or after impregnating the rhodium or palladium compound or mixture thereof on the support. Such a composition when used as a catalyst is regenerated by air burn-off and is a highly active and selective catalyst. Further, treatment of the composition with a halogen-containing compound improves the selectivity of the catalyst.

Further according to the invention a composition comprises at least one rhodium or palladium compound or mixture thereof supported on a calcined, acidic, nickel and rare earth-treated crystalline zeolite.

Further according to the invention the above composition is prepared by contacting a crystalline zeolite with an aqueous cation exchange solution comprising rare earth, nickel and ammonium compounds; removing the zeolite from said solution and washing said zeolite with water to remove excess ions; calcining said cation exchanged zeolite; cooling said calcined zeolite; and impregnating said cation exchanged zeolite before or after said calcination step with a solution comprising at least one rhodium or palladium compound or mixture thereof in a suitable solvent and removing said solvent by evaporation. The acidity of the above composition is easily adjusted by varying the conditions under which the cation exchange step is carried out, such as, for example, adjusting the concentration of an ammonium compound in the cation exchange solution.

DETAILED DESCRIPTION OF THE INVENTION

The composition of the instant invention can be briefly described as a crystalline zeolite which has been cation exchanged with rare earth, nickel and ammonium compounds followed by a calcination step and a rhodium or palladium compound impregnation step wherein the rhodium or palladium compound or mixture thereof is impregnated on the cation exchanged zeolite to give the final composition either before or after the calcination step. Although not absolutely necessary, it is preferred that the above catalyst be treated with hydrogen prior to introduction of the aromatic hydrocarbon feed in the hydroalkylation process because of improved results.

The compositions of the instant invention are useful as catalysts and to some extent solve or obviate each of the above-mentioned deficiencies of the prior art catalyst. For example, the supports utilized for the compositions of the instant invention are stable to regeneration conditions utilized under typical air burn-off operations; they appear to operate at higher levels of productivity in that they show a higher degree of activity and selectivity than certain of the prior art catalysts; the process of making the compositions of the instant invention is simple and straightforward and the compositions thus obtained should be less expensive than those of the prior art which utilize very complex steps in their preparation; and the compositions of the instant invention can be made with a high degree of flexibility in the degree of acidity simply by adjusting the cation exchange conditions on the crystalline zeolite support utilized for the compositions of this invention.

The support material for the composition employed in the instant invention is a crystalline zeolite which has been treated under cation exchange conditions with a mixture of rare earth, nickel and ammonium compounds such that the cation metal content of the support is partially exchanged. Generally the cationic metal is an alkali metal which is sufficiently removed by cation exchange such that the remaining alkali metal content after the cation exchange step ranges from about 0.01 to about 2 percent by weight; however, the runs carried out in accordance with the invention and reported herein indicate that good results can be obtained when the alkali metal content of the cation exchanged zeolite ranges from about 0.1 to about 1 percent by weight. Some of the more commonly employed crystalline zeolites which are suitable for use in accordance with the present invention are the Type X or Type Y crystalline zeolites which are sometimes called molecular sieves because of their essentially uniform pore diameters. Some suitable Type Y synthetic crystalline zeolites are described for example in U.S. Pat. No. 3,130,007 and some suitable Type X zeolites are described in U.S. Pat. No. 2,882,244. Such materials are presently commercially available as for example zeolites SK-40 (Type Y) and 13X (Type X) from the Linde Division of Union Carbide Corporation, New York, New York.

The alkali metal form of the crystalline zeolites usually comprises sodium as the alkali metal and said zeolites are treated under cation exchange conditions with a mixture of rare earth, nickel and ammonium compounds in accordance with the present invention in order to provide a suitable support material for use in the preparation of the compositions of the invention.

It is contemplated that any of the readily available rare earth metal compounds may be employed in the cation exchange solution. Generally, the compounds used are those in which the rare earth metal-containing ion is present in the cationic state. Representative rare earth metal compounds include nitrates, bromides, acetates, chlorides, iodides, sulfates and mixtures thereof of one or more of the rare earth metals including cerium, lanthanum, praseodymium, neodymium, samarium, europium, gadolinium, terbium, dysprosium, holmium, erbium, thulium, ytterbium, and lutetium. Compounds of the rare earths named above may be employed singly; however, it is often convenient to employ mixtures of the rare earths as these are commercially available. For example, mixtures of rare earth metal compounds such as the chlorides of lanthanum, cerium, praseodymium, neodymium, samarium and gadolinium are available commercially at a relatively low cost and may be effectively employed.

As noted above, the zeolite material is cation exchanged with a mixture of rare earth, nickel and ammonium compounds according to the instant invention. Any convenient ammonium compound may be employed although the chloride is preferred because it is inexpensive and readily available. The weight ratio of ammonium compound to nickel and rare earth compounds in the aqueous exchange solution can be selected over a broad range. Generally the weight ratio of ammonium compound to nickel and rare earth compounds combined is within the range of from about 0.05:1 to about 20:1, although the data contained herein indicates that a range of from about 0.2:1 to about 5:1 can be used with good results. The concentration of rare earth compounds in the aqueous exchange solution can be varied over a wide range and exchange conditions can be adjusted accordingly such that the rare earth content of the ion exchanged crystalline zeolite can be selected over a broad range. Generally, the content of the final catalyst composite in terms of the rare earth elements is from about 2 to about 25 weight percent. The runs described herein indicate that the rare earth content of the catalyst can be within the range of from 5 to 20 weight percent. Good results were obtained employing a rare earth content ranging from about 9 to about 11 percent by weight. As noted above, the alkali metal content, for example sodium, of the exchanged catalyst support is partially removed by the ion exchange step and the alkali metal is generally from about 0.01 to about 2 percent by weight; however, the runs described herein indicate that good results can be obtained employing an alkali metal content ranging from about 0.1 to about 1 percent by weight.

The nickel compounds which will be employed in admixture with the above-named rare earth metal compounds and ammonium compounds are those wherein the nickel ion is present in the cationic state. Some suitable compounds representative of the nickel compounds which can be used in the invention include the nitrates, bromides, acetates, chlorides, iodides, sulfates and mixtures thereof.

The nickel content in the final composition can also be selected over a broad range. Generally the composition will comprise from about 0.01 to about 12 weight percent nickel, although the runs carried out in accordance with the invention and described herein indicate that good results can be obtained employing a nickel content ranging from about 2 to about 7 percent by weight. These runs were actually carried out in which the nickel content ranged from about 4 to about 6 weight percent.

The procedure whereby the Type X and Type Y zeolites are treated with aqueous solutions of rare earth, nickel and ammonium compounds to replace a portion of the alkali metal content of the zeolite is a cation exchange process which can be carried out in a batch or continuous fashion. Generally the exchange process is carried out on a continuous basis under the following typical conditions. A fixed bed of the zeolite material is treated with said aqueous solution of the rare earth, nickel and ammonium compounds at a temperature of 90° to 110° C under conditions such that from about 0.1 to about 0.5 of the volume of aqueous salts solution per volume of zeolite is in contact with said zeolite per hour or, in other words, an LHSV ranging from about 0.1 to about 0.5 is employed in the exchange process. Under these conditions, the exchange process can be completed in 48 hours or less to achieve the desired level of rare earth, nickel and ammonium ions in the zeolite. The exchanged zeolite is then washed free of excess ions from the exchange step with water. The excess wash water is removed by drying the zeolite at a temperature ranging from about 100° to about 300° C just prior to calcination. The instant catalyst can be calcined before impregnation with the rhodium or palladium compound to be described below or the impregnation can be carried out prior to the calcination step. In either case, the calcination is carried out by slowly heating the zeolite from about 100° to 200° C to a temperature within the range of from about 200° to about 550° C in order to calcine the zeolite and convert the ammonium cations to the hydrogen form. Usually, the calcination is conducted until a constant weight is obtained for the zeolitic material, generally from about 2 to about 10 hours. The calcined zeolite is then cooled in ambient air, i.e., under conditions of normal humidity.

The above-described support is impregnated with a solution of at least one rhodium or palladium compound or mixture thereof followed by evaporation of the solvent used in the impregnation step. Evaporation of the solvent can be conducted under vacuum if desired. Suitable solvents include water, alcohols, such as ethanol, ketones, such as acetone, and the like. Some of the various rhodium or palladium compounds suitable for use in the impregnation step include rhodium(III) acetylacetonate, rhodium(I) dicarbonyl chloride dimer, rhodium(III) nitrate, and rhodium(III) trichloride, palladium(II) acetylacetonate, palladium(II) chloride, palladium(II) iodide, and palladium(II) nitrate. The impregnation is generally carried out under what may be called "total impregnation" whereby the entire solids in the solutions used in the impregnation are left on the catalyst support and the liquid solvent for said compounds is simply removed by evaporation.

The rhodium and/or palladium content in the final composition can be selected over a broad range. Generally the rhodium and/or palladium content ranges from 0.01 to about 1 percent by weight although the runs described herein indicate that good results can be obtained employing a rhodium and/or palladium content within the range from about 0.05 to 0.25 percent by weight. No actual runs were carried out in which a mixture of rhodium and palladium compounds were used; however, there is no reason to believe that such mixtures are not operable and thus within the scope of the present invention.

The composition described above is employed for the hydroalkylation of aromatic hydrocarbons to produce cycloalkyl aromatic hydrocarbons. Some of the feedstocks which are suitable for use in the present invention are aromatic compounds, i.e., monocyclic aromatic hydrocarbons and alkyl-substituted monocyclic aromatic hydrocarbons. Some specific examples of these are benzene, toluene, xylenes, and the like, and mixtures thereof. The aromatic hydrocarbon feedstocks should be essentially free of sulfur-containing compounds and other known poisons for hydrogenation catalysts in general. However, it is believed that a small amount of water, e.g., 20–50 ppm, in the feedstock is beneficial for maintaining catalyst activity over an extended period, e.g., several days.

The invention is particularly valuable for the conversion of benzene to cyclohexylbenzene. Cyclohexylbenzene is known as a valuable solvent and chemical intermediate. It can be converted in high yield to phenol and cyclohexanone by autooxidation with subsequent acid treatment. It is also useful as an intermediate in the production of cyclohexene which in turn can be utilized for the production of adipic acid and caprolactam.

The aromatic hydrocarbon feedstock is fed to the catalyst in a reaction zone operated under a wide range of conditions. The feedstock liquid hourly space velocity (LHSV), reaction temperature and pressure, and the hydrogen feed rate are not particularly critical; however, the liquid hourly space velocity (LHSV) generally ranges from about 1 to about 100, the reaction pressure generally ranges from about 345 to about 10,350 kPa (about 50 to about 1500 psig), the hydrogen feed rate generally ranges from about 0.1 to about 10 mole per mole of aromatic hydrocarbon feedstock per hour, and the reaction temperature generally ranges from about 100° to about 250° C. Based upon the runs described herein good results can be obtained employing a liquid hourly space velocity (LHSV) within the range of from about 5 to about 30, a reaction pressure within the range of from about 1,380 to about 4,830 kPa (about 200 to about 700 psig), the hydrogen feed rate within the range of from about 0.2 to about 1 mole per mole of aromatic hydrocarbon feed per hour, and the reaction temperature within the range of from about 140° to about 200° C.

The hydroalkylation reaction is conveniently carried out by having the above-described catalyst in a fixed bed reactor and then contacting said catalyst with the aromatic hydrocarbon feed and hydrogen in an upflow or downflow arrangement. It is also possible to employ a countercurrent flow of hydrogen and the aromatic hydrocarbon feed over the catalyst in the reaction zone. It is also possible to carry out the hydroalkylation reaction under batch conditions although a batch process is less preferred, because it is normally more expensive to operate and initial equipment costs are higher based upon the same size process.

Although a fixed bed reactor is mentioned above, most any type of reaction zone can be used as the particular type of reaction zone is not believed to be a critical parameter of the invention.

The reaction mixture from the reaction zone can usually be conveniently separated into the desired components by simple fractional distillation, and recycle of the unreacted feedstock and unreacted hydrogen can be accomplished as desired. The hydroalkylation products can be further purified as desired after separation from unreacted feedstock.

It is generally desirable to pretreat the catalyst with hydrogen gas prior to contacting the catalyst with the aromatic hydrocarbon in order to prereduce the catalyst. Based upon the runs described hereinafter, the hydrogen pressure and feed rate for the pretreating step generally is the same as that to be employed when contacting the aromatic hydrocarbon with the catalyst and the pretreating step generally takes from about 10 minutes to about 1 hour. In the hydroalkylation runs of the examples hereinafter described, conditions under which the catalyst was reduced and the reaction was carried out are indicated.

Further according to another aspect of the invention the catalysts as above described are treated with a small amount of a halogen-containing compound. Such a treatment of the catalyst compositions of the present invention was found to improve the selectivity of such compositions in hydroalkylation reactions. The compounds which can be utilized according to the instant invention as a source of halide include the elemental halogens themselves and the hydrohalides. Since treatment of the catalyst compositions of the invention with a compound as described above generally requires careful control of the addition reaction, it is preferred to employ a halogen-containing organic compound to treat the catalyst composition of the instant invention. A wide variety of such organic compounds can be employed to provide the necessary halide in the instant invention. These compounds can contain one or more atoms of halogen per molecule and the carbon content of such compounds is generally in the range of from about 1 to about 4 carbon atoms per molecule. For example, such compounds include alkyl halides, acid halides, or fully halogenated carbon compounds such as carbon tetrachloride or tetrachloroethylene. Examples of other suitable organic compounds which can be employed include chloroform, bromoform, dichloromethane, difluoromethane, dibromomethane, fluoromethane, chloromethane, bromomethane, 1,4-dichlorobutane, 1,4-dibromobutane, 1-chlorobutane, 1-fluorobutane, 1-bromobutane, 1,2-dichloroethane, 1,2-dibromoethane, 2-chloropropane, acetyl chloride, acetyl bromide, acetyl iodide, bromochloromethane, 1-bromo-4-chlorobutane, 1-fluoro-4-chlorobutane, 1,2-dichloroethylene, 1,2-dibromoethylene and mixtures thereof. Based upon the results of the runs demonstrating this aspect of the invention described herein, the halogen-containing organic compounds in which the halogen component is bromine or chlorine are preferred.

Although the catalysts of the present invention can be treated with halogen-containing compounds in various ways, one method which has been successfully employed is to simply add said halogen-containing compound to the aromatic hydrocarbon feed in the hydroalkylation process. The amount of halide added to the catalyst generally ranges from about 0.1 to about 100 milligrams of the elemental halogen per gram of catalyst utilized in the hydroalkylation reaction; however, based upon the results of the runs herein, good results can be obtained employing from about 0.5 to about 10 milligrams of the elemental halogen per gram of catalyst employed in the hydroalkylation reaction.

The addition of the halogen-containing compounds to the aromatic hydrocarbon feedstream can be utilized when the catalyst is fresh, i.e. previously unused, or can also be utilized after one or more regenerations of the above-mentioned catalyst. A typical regeneration procedure for the above-described catalyst includes purging the system of hydrogen with an inert gas such as nitrogen, then allowing air to enter the reaction zone and heating to a range of from about 400° to about 500° C in the presence of flowing air and maintaining this temperature in the presence of flowing air for a total time of about three hours. The catalyst is then cooled in the presence of flowing air or nitrogen and at a temperature of about 200° C is reduced with hydrogen as above described. The catalyst is then cooled to the desired reaction temperature and is then ready for use in the hydroalkylation reaction.

Although the compound or compounds which serve as the source of halide to modify the hydroalkylation catalyst of this invention can be added to the hydrocarbon feed in one portion, good results were obtained by adding the halogen-containing compound to the feed over a period of from about 1 to about 3 hours. It is believed that a more efficient utilization of the halogen-containing compound is achieved by the above-described gradual addition of said compounds to the hydrocarbon feed in the process of this invention. It is to be understood that the halide treatment of the catalyst generally is only for a limited period of time and that the catalyst is then contacted with the feed in which no halogen-containing compound is added.

EXAMPLES

EXAMPLE I

Catalyst Preparation

The catalyst utilized in the runs of this example, designated catalyst No. 1, was prepared in the following manner. A glass tube of 45 mm diameter, which was equipped with heating means and means for passing an aqueous solution of compounds therethrough was charged with 200 grams of a type X crystalline zeolite (Davison 13X mole sieves of 8 to 12 mesh). An aqueous solution of 400 grams of ammonium chloride, 100 grams of rare earth chlorides, and 200 grams of nickel chloride hexahydrate in 4 liters of deionized water was prepared. The rare earth chlorides were utilized as a commercially available mixture having the following composition: $MCl_3 \cdot 6H_2O$ wherein M = lanthanum 23%, cerium 43.5%, praseodymium 5.4%, neodymium 17.9%, samarium 1.9%, gadolinium 0.6%, and others 0.2%. The crystalline zeolite material was first wetted with a portion of the above solution and then charged to the tubular glass reactor described above and the remainder of the aqueous solution pumped through the crystalline zeolite bed, the material was cooled, filtered, and washed six times with 350 ml portions of water and then allowed to dry in ambient air. A portion (27.3 grams) of the cation-exchanged crystalline zeolite was then treated with a solution of 0.033 gram of $PdCl_2$ in 25 ml $H_2O$ and about 3 ml of aqueous $NH_3$. The impregnated crystalline zeolite material was dried under vacuum to give a weight of 26.5 grams of the zeolite material. This material was then calcined by heating for about 4 hours in a furnace to about 205° C (400° F) and then the temperature increased slowly up to about 524° C (975° F) over an 8-hour period and then allowed to cool in the air. The catalyst thus prepared contained 0.1% palladium, 4.68% nickel, about 9.5% rare earths, and about 0.63% sodium by weight.

Benzene Hydroalkylation

Catalyst No. 1 described above was utilized in the hydroalkylation of benzene. In these hydroalkylation runs, a small tubular reactor equipped for continuous reaction operation was charged with 10 grams (13 ml) of the catalyst. The catalyst was prereduced at 150° C under 3,450 kPa (500 psig) hydrogen at a flow rate of 0.32 liter per minute of hydrogen for a period of 15 minutes. Hydrogen pressure and flow rate during these runs were the same as utilized in the prereduction step. After the reaction system had reached the desired operating conditions, samples of the reactor effluent were taken for analysis by gas-liquid phase chromatography to provide the data shown below in Table I. Other reaction conditions are also shown with the results obtained in Table I.

Table I

| Run No. | Temp. ° C | Benzene LHSV | Benzene Conv.% | Selectivity, Wt.% CH[a] | Selectivity, Wt.% CHB[b] | Weight Ratio CHB/CH |
|---|---|---|---|---|---|---|
| 1 | 183 | 8.4 | 4.4 | 34.1 | 59.2 | 1.7 |
| 2 | 193 | 7.7 | 3.4 | 32.4 | 67.6 | 2.1 |
| 3 | 190 | 4.6 | 1.3 | 53.7 | 46.2 | 0.9 |

[a]CH = cyclohexane.
[b]CHB = cyclohexylbenzene.

The above runs demonstrate the operability of a composition of the invention employed as a catalyst in a benzene hydroalkylation reaction.

EXAMPLE II

Catalyst Preparation

Another catalyst (No. 2) was prepared and utilized according to the instant invention in a benzene hydroalkylation run. In the preparation of the catalyst, 350 grams of a type X crystalline zeolite (Davison 13X molecular sieves, Grade 544, 8-12 mesh) was treated with a slow stream of air over a 2-day period. Following this treatment, the above material weighed 424 grams. A solution of 400 grams of ammonium chloride, 200 grams of nickel chloride hexahydrate and 100 grams of the rare earth chloride mixture utilized in the previous example, in 4 liters of deionized water was prepared. The crystalline zeolite material was wetted with the above solution and then charged to the cation exchange reactor previously described which, in this instance, also had a bottom bed of about 100 ml of 6 mm diameter glass beads. The cation exchange solution was pumped over the crystalline zeolite bed at a temperature of about 95° C at a liquid hourly space velocity of about 0.25. The material was cooled, filtered, and washed six times with about 500 ml portions of deionized water and then allowed to dry in ambient air. The recovered cation-exchanged crystalline zeolite weighed 512.3 grams. A portion (36.5 grams) of the above-described cation-exchanged zeolite was impregnated with 25 grams of a solution of palladium chloride in aqueous hydrochloric acid (1,000 ppm palladium as palladium chloride in HCl). However, the hydrochloric acid was neutralized with ammonium hydroxide before the impregnation was carried out. The water was removed under reduced pressure on a rotary evaporator. Zeolite material adhering to the sides of the flask was washed once with water and then with ethanol. Each time the wash solvent was removed on a rotary evaporator. The residue recovered was placed in an oven and calcined in the presence of flowing air by first maintaining the zeolite in the oven at 24° C (75° F) and then gradually increasing the temperature during the overnight period to 205° C (400° F) followed by an increase in temperature to 471° C (880° F) over an 8-hour period. After cooling, the recovered catalyst was placed in a sealed bottle. The catalyst thus prepared contained 0.1% palladium, 4.68% nickel, about 9.5% rare earths, and about 0.63% sodium by weight.

Benzene Hydroalkylation

Catalyst No. 2 described above was utilized in the hydroalkylation of benzene in the runs described below in Table II. In these hydroalkylation runs, a small tubular reactor equipped for continuous reaction operation was charged with 11.2 grams (15 ml) of the catalyst. The catalyst was prereduced at 200° C under 3,450 kPa (500 psig) hydrogen at a flow rate of 0.19 liters per minute of hydrogen for a period of 2 hours. Run 6 in Table II below was carried out after the catalyst had been regenerated by a burn-off in flowing air at 510° C for a period of about 2.33 hours. The data in Runs 7 to 9 of Table II was obtained after the catalyst was treated with a benzene feed admixed with 50 ppm of carbon tetrachloride for 1.8 hours and the feed was switched back to pure benzene. Other reaction conditions and the results obtained in the hydroalkylation runs are shown in Table II.

Table II

| Run No. | Temp. °C | Benzene LHSV | Benzene Conv.% | Selectivity, Wt.% CH | Selectivity, Wt.% CHB | Weight Ratio CHB/CH |
|---|---|---|---|---|---|---|
| 4[a] | 171 | 20 | 14.6 | 22.9 | 70.9 | 3.1 |
| 5[b] | 173 | 20 | 9.5 | 20.6 | 72.3 | 3.5 |
| 6[a] | 174 | 20 | 16.8 | 17.6 | 75.8 | 4.5 |
| 7[b] | 169 | 20 | 6.2 | 11.7 | 80.7 | 6.9 |
| 8[b] | 155 | 16.7 | 7.1 | 12.9 | 81.1 | 6.3 |
| 9[c] | 169 | 20 | 8.5 | 7.6 | 85.4 | 11.3 |

[a]Hydrogen pressure of 3,450 kPa and 760 GHSV.
[b]Hydrogen pressure of 2,070 kPa and 320 GHSV.
[c]Hydrogen pressure of 2,070 kPa and 1520 GHSV.

The above runs demonstrate the operability of the invention. A comparison of the results of Run 6 with Runs 4 and 5 shows that the regenerated catalyst, under the conditions employed, is more active. Runs 7, 8 and 9, carried out with a halogen-treated catalyst, show improved selectivity as compared to Runs 4, 5 and 6 although the activity is somewhat lower as indicated by the lower conversion values.

EXAMPLE III

Catalyst Preparation

Catalyst No. 3 was prepared utilizing the same cation-exchanged catalyst support of catalyst No. 1 of Example I. A portion (27.3 grams) of the cation-exchanged support was impregnated under total impregnation conditions with a solution of 0.050 gram of $RhCl_3$ in 25 ml water. The impregnated crystalline zeolite material was dried under vacuum to give 27.7 grams of the material. The impregnated catalyst material was calcined under the same conditions utilized for the preparation of catalyst No. 1. The catalyst thus prepared contained 0.1% rhodium, 4.68% nickel, about 9.5% rare earths, and about 0.63% sodium by weight.

Benzene Hydroalkylation

Catalyst No. 3 described above was utilized in benzene hydroalkylation runs. In these runs, a small tubular reactor equipped for continuous reaction operation was charged with 10 grams (14 ml) of catalyst No. 3. The catalyst was prereduced at 150° C under 3,450 kPa (500 psig) hydrogen at a flow rate of 0.32 liter per minute for a period of 15 minutes. The temperature employed during these runs was 178° C. Other reaction conditions and the results obtained in the hydroalkylation runs are shown in Table III.

Table III

| Run No. | H₂ Press., kPa | Benzene LHSV | Benzene Conv.% | Selectivity, Wt.% CH | Selectivity, Wt.% CHB | Weight Ratio CHB/CH |
|---|---|---|---|---|---|---|
| 10 | 3450 | 15.7 | 9.0 | 31.4 | 56.5 | 1.8 |
| 11 | 3450 | 7.1 | 13.6 | 37.7 | 60.3 | 1.6 |
| 12[a] | 2070 | 7.1 | 6.3 | 14.3 | 71.4 | 5.0 |

[a]Run made after 50 ppm carbon tetrachloride was admixed with the benzene feed for 3 hours.

Runs 10, 11 and 12 demonstrate operability of the invention. Run 12 shows improved selectivity from the halide treatment of the catalyst.

EXAMPLE IV

Catalyst Preparation

Catalyst Nos. 4 and 5 were prepared in essentially the same manner as that described for the preparation of catalyst No. 3 above to provide hydroalkylation catalysts having a rhodium content of 0.1 weight percent, nickel content of 4.68 weight percent, rare earth content of about 9.5 weight percent and a sodium content of about 0.63 weight percent. Catalyst No. 4 was not calcined prior to charging to the reactor while catalyst No. 5 was calcined by gradually increasing the temperature from 24° C (75° F) to 205° C (400° F) overnight then increasing the temperature to (510° C) 950° F over an 8-hour period. These catalysts prepared as described above were utilized in benzene hydroalkylation runs.

Benzene Hydroalkylation

In the runs utilizing catalyst No. 4, Runs 13–15, the small tubular reactor equipped for continuous operation was charged with 13.3 grams (15 ml) of the catalyst. The catalyst was first heated to 500° C and held at this temperature in flowing air for a period of about 2 hours. The catalyst chamber was then cooled under flowing nitrogen and the catalyst then prereduced at about 300° C under 3,450 kPa (500 psig) hydrogen at a flow rate of 0.32 liter per minute for 1 hour. The temperature was further reduced prior to charging the benzene feed to the reaction zone. The runs utilizing catalyst No. 5, Runs 16 to 18, were carried out by charging the small tubular reactor for continuous operation with 11.1 grams (15 ml) of the catalyst. The catalyst was prereduced at about 175° C under 2,070 kPa (300 psig) hydrogen at a flow rate of 4 liters per minute for a period of 30 minutes. Data for runs 14, 15, 17 and 18 was obtained utilizing benzene feed but after the catalysts had been used for hydroalkylation of benzene feed admixed with 50 ppm carbon tetrachloride for periods of about 1–3 hours. Other reaction conditions and the results obtained in the hydroalkylation runs with catalyst Nos. 4 and 5 are shown below in Table IV.

Table IV

| Run No. | Cat. No. | Temp. °C | Benzene LHSV | Benzene Conv.% | Selectivity Wt.% CH | Selectivity Wt.% CHB | Weight Ratio CHB/CH |
|---|---|---|---|---|---|---|---|
| 13[a] | 4 | 180 | 17.0 | 8.6 | 20.2 | 68.6 | 3.4 |
| 14[a] | 4 | 178 | 20 | 7.9 | 12.4 | 81.8 | 6.6 |
| 15[b] | 4 | 180 | 20 | 9.6 | 20.4 | 69.4 | 3.4 |
| 16[a] | 5 | 173 | 20 | 8.4 | 27.9 | 61.4 | 2.2 |
| 17[a] | 5 | 173 | 20 | 7.0 | 13.6 | 80.1 | 5.9 |
| 18[c] | 5 | 174 | 20 | 14.6 | 19.4 | 69.8 | 3.6 |

[a]Hydrogen pressure of 2,070 kPa (300 psig) at a flow rate of 0.21 liter per minute.
[b]Hydrogen pressure of 3,450 kPa (500 psig) at a flow rate of 0.21 liter per minute.
[c]Hydrogen pressure of 3,450 kPa (500 psig) at a flow rate of 0.32 liter per minute.

The runs further demonstrate the operability of the invention.

EXAMPLE V

Catalyst Preparation

Catalyst No. 6 was also prepared in essentially the same manner as that described for catalyst No. 3 above except that the amount of nickel chloride hexahydrate in the cation exchange solution was 100 grams and the rare earth chlorides was 200 grams per 4 liters of the cation exchange solution. After impregnation of the cation-exchanged catalyst with the rhodium compound $Rh(NO_3)_3$ under conditions similar to those employed in the preparation of catalyst No. 3, the catalyst was not calcined prior to use in hydroalkylation runs. Catalyst No. 6 thus prepared contained 0.1% rhodium and 2.6% nickel, about 14% rare earths, and about 0.63% sodium by weight. Catalyst No. 7 was also prepared in a manner similar to that utilized in the preparation of catalyst No. 3. However, the amount of rhodium in the catalyst was reduced to one-half the amount previously utilized in the above-described catalyst. Catalyst No. 7 thus prepared contained 0.05% rhodium, 2.1% nickel, about 12.5% rare earths, and about 0.98% sodium by weight.

Benzene Hydroalkylation

Catalyst Nos. 6 and 7 described above were utilized in benzene hydroalkylation runs. Both catalyst were prereduced at 150° C under 3,450 kPa (500 psig) hydrogen at a flow rate of 0.32 liter per minute for 15 minutes. Hydrogen pressure and flow rate during the hydroalkylation runs were maintained at these levels. Other reaction conditions and the results obtained in the hydroalkylation runs are shown below in Table V.

Table V

| Run No. | Cat. No. | Temp. °C | Benzene LHSV | Benzene Conv.% | Selectivity Wt.% CH | Selectivity Wt.% CHB | Weight Ratio CHB/CH |
|---|---|---|---|---|---|---|---|
| 19 | 6 | 175 | 8.3 | 12.0 | 33.0 | 56.1 | 1.7 |
| 20 | 7 | 180 | 10 | 2.7 | 33.6 | 57.2 | 1.7 |

Runs 6 and 7 demonstrate operability of the present invention although the activity and selectivity of these catalysts is not as high as some of the catalysts of the previous runs under the conditions employed.

EXAMPLE VI

Catalyst Preparation

Catalyst No. 8 is a control catalyst in that said catalyst composition does not contain rhodium or palladium as a catalyst component. In effect, catalyst No. 8 is a cation-exchanged crystalline zeolite of Type X previously utilized as the support material for the catalysts of the instant invention. In this instance, the cation exchange process was carried out using 250 grams of Davison Chemical 13X molecular sieves and 4 liters of a solution of 400 g $NH_4Cl$, 400 g $NiCl_2.6H_2O$ and 100 g of the previously employed mixed rare earth chlorides in deionized water. The exchange process was carried out at about 100° C and at about 0.25 LHSV. The cation-exchanged material was washed 6 times with 350 ml portions of water and dried in air. One-half of the product (141.8 g) was calcined in the manner previously described to an upper temperature of 513°C (955° F). Catalyst No. 8 thus prepared contained 6.5% nickel, about 9.5% rare earths, and 0.72% sodium by weight.

Benzene Hydroalkylation

Catalyst No. 8 described above was utilized in a benzene hydroalkylation run in the continuous reaction system previously described. In this run, the reaction chamber was charged with 15.8 grams (20 ml) of catalyst No. 8, and the catalyst was prereduced at 300° C under 3,450 kPa (500 psig) hydrogen at a flow rate of 0.32 liter per minute. The hydrogen pressure and flow rate were maintained at these levels during the hydroalkylation run. Other reaction conditions and the results obtained in the hydroalkylation run are shown in Table VI.

Table VI

| Run No. | Temp. °C | Benzene LHSV | Benzene Conv.% | Selectivity Wt.% CH | Selectivity Wt.% CHB | Weight Ratio CHB/CH |
|---|---|---|---|---|---|---|
| 21 | 213 | 5 | 4.0 | 36.3 | 54.5 | 1.5 |

The results of run 21 demonstrate that without a palladium or rhodium component the catalyst even at a relatively high temperature and low liquid hourly space velocity is very poorly suited for benzene hydroalkylation to cyclohexylbenzene. This is evidenced by the low benzene conversion and relatively poor selectivity to cyclohexylbenzene.

What is claimed is:

1. A process for producing monocycloalkyl aromatic hydrocarbons comprising:
contacting an aromatic hydrocarbon under hydroalkylation conditions and in the presence of hydrogen with a catalyst comprising at least one component selected from the group consisting of rhodium and palladium compounds and mixtures thereof supported on a calcined, acidic, nickel and rare earth-treated crystalline zeolite selected from the Group consisting of Type X and Type Y zeolite.

2. The process of claim 1 wherein the total rhodium and palladium content ranges from about 0.01 to about 1 percent by weight.

3. The process of claim 1 wherein the total rhodium and palladium content ranges from about 0.05 to about 0.25 percent by weight.

4. The process of claim 1 wherein the crystalline zeolite is selected from the group consisting of Type X and Type Y zeolites;
 wherein the rare earth metal and nickel compounds are selected from the group consisting of nitrates, bromides, acetates, chlorides, iodides, sulfates and mixtures thereof;
 wherein the rare earth metal is selected from the group consisting of cerium, lanthanum, praseodymium, neodymium, samarium, europium, gadolinium, terbium, dysprosium, holmium, erbium, thulium, ytterbium, lutetium and mixtures thereof, and
 wherein the rhodium and palladium compounds are selected from the group consisting of rhodium(III) acetylacetonate, rhodium(I) dicarbonyl chloride dimer, rhodium(III) nitrate, and rhodium(III) trichloride, palladium(II) acetylacetonate, palladium(II) chloride, palladium(II) iodide, palladium(II) nitrate and mixtures thereof.

5. The process of claim 1 wherein the crystalline zeolite is the alkali metal form with the alkali metal content of the calcined, acidic, nickel and rare earth-treated crystalline zeolite in the range of from about 0.01 to about 2 percent by weight;
 wherein the rare earth content of the calcined acidic, nickel and rare earth-treated crystalline zeolite ranges from about 2 to about 25 percent by weight; and
 wherein the nickel content of the calcined, acidic, nickel and rare earth-treated crystalline zeolite ranges from about 0.01 to about 12 percent by weight.

6. The process of claim 1 wherein the crystalline zeolite is the alkali metal form with the alkali metal content of the calcined, acidic, nickel and rare earth-treated crystalline zeolite in the ranges of from about 0.05 to about 1 percent by weight;
 wherein the rare earth content of the calcined, acidic, nickel and rare earth-treated crystalline zeolite ranges from about 5 to about 20 percent by weight; and
 wherein the nickel content of the calcined, acidic, nickel and rare earth-treated crystalline zeolite ranges from about 2 to about 7 percent by weight.

7. The process of claim 1 wherein the catalyst is treated with hydrogen prior to being contacted with the monocyclic aromatic hydrocarbon.

8. The process of claim 1 wherein the monocyclic aromatic hydrocarbon is contacted with said catalyst at a liquid hourly space velocity ranging from about 1 to about 100, a hydrogen pressure ranging from about 345 to about 10,350 kilopascals 50 to 1500 psig), a hydrogen feed rate ranging from about 0.1 to about 10 moles per hour of hydrogen per mole of monocyclic aromatic hydrocarbon, and a temperature ranging from about 100° to about 250° C.

9. The process of claim 1 wherein the monocyclic aromatic hydrocarbon is contacted with said catalyst at a liquid hourly space velocity ranging from about 5 to about 30, a hydrogen pressure ranging from about 1380 to about 4830 kilopascals (200 to 700 psig), a hydrogen feed rate ranging from about 0.2 to about 1 mole of hydrogen per mole of monocyclic aromatic hydrocarbon per hour, and a temperature ranging from about 140° to about 200° C.

10. The process of claim 1 wherein the crystalline zeolite is selected from the group consisting of Type X and Y zeolites; and
 the rhodium and palladium compounds are rhodium chloride and palladium chloride respectively, the nickel compound used to treat the crystalline zeolite is nickel chloride hexahydrate and the rare earth metal compound used to treat the crystalline zeolite is a mixture of the chlorides of at least lanthanum, cerium, praseodymium, neodymium, samarium and gadolinium.

11. The process of claim 1 wherein the catalyst is treated with a halogen-containing compound in an amount sufficient to promote the formation of a desired cycloalkyl aromatic hydrocarbon when said composition is employed in a hydroalkylation reaction.

12. The process of claim 1 wherein the catalyst is treated with a halogen-containing compound in an amount ranging from about 0.1 to about 100 milligrams of the elemental halogen per gram of said composition.

13. The process of claim 1 wherein the catalyst is treated with an organic halogen-containing compound and the amount of said organic halogen-containing compound ranges from about 0.5 to about 10 milligrams of the elemental halogen per gram of the catalyst employed.

14. The process of claim 1 wherein the catalyst is treated with a halogen-containing compound selected from the group consisting of carbon tetrachloride, tetrachloroethylene, chloroform, bromoform, dichloromethane, difluoromethane, dibromomethane, fluoromethane, chloromethane, bromomethane, 1,4-dichlorobutane, 1,4-dibromobutane, 1-chlorobutane, 1-fluorobutane, 1-bromobutane, 1,2-dichloroethane, 1,2-dibromoethane, 2-chloropropane, acetyl chloride, acetyl bromide, acetyliodide, bromochloromethane, 1-bromo-4-chlorobutane, 1-fluoro-4-chlorobutane, 1,2-dichloroethylene, 1,2-dibromoethylene and mixtures thereof.

* * * * *